Figure 1A:
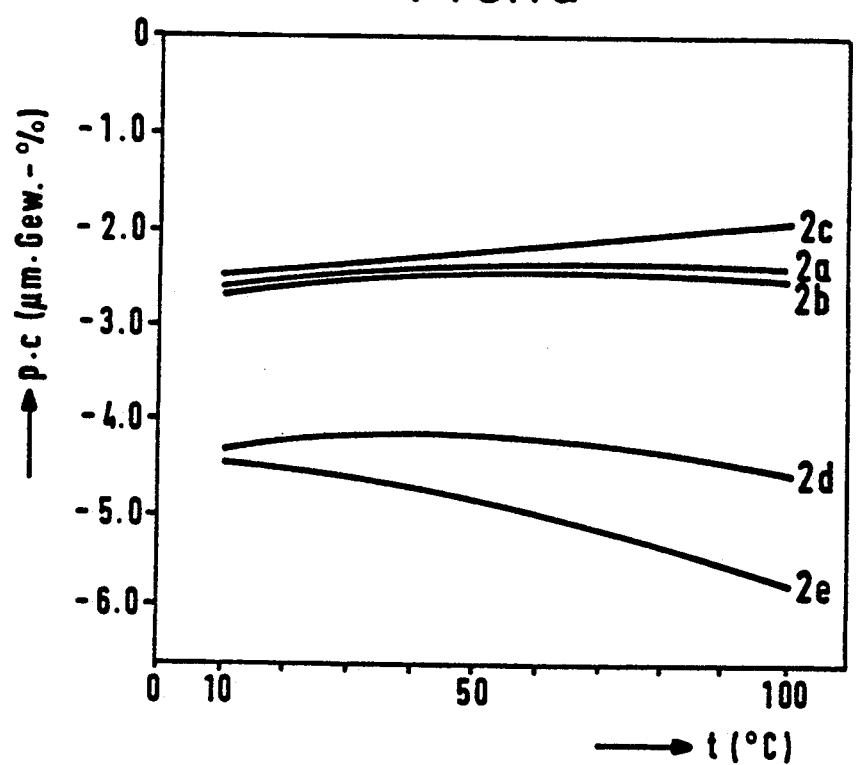

United States Patent [19]

Scherowsky et al.

[11] Patent Number: 4,996,330

[45] Date of Patent: Feb. 26, 1991

[54] CHIRAL SUBSTITUTED TARTARIMIDES

[75] Inventors: Günter Scherowsky, Berlin; Peter Schreiber, Berlin, both of Fed. Rep. of Germany

[73] Assignee: Hoechst Aktiengesellschaft, Frankfurt am Main, Fed. Rep. of Germany

[21] Appl. No.: 373,179

[22] Filed: Jun. 28, 1989

[30] Foreign Application Priority Data

Jun. 30, 1988 [DE] Fed. Rep. of Germany ....... 3822121

[51] Int. Cl.$^5$ .......................................... C07D 207/416
[52] U.S. Cl. ..................................... 548/544; 548/547
[58] Field of Search .................................. 548/547, 544

[56] References Cited

U.S. PATENT DOCUMENTS 4,237,022 12/1980 Barrer ................................. 548/544

FOREIGN PATENT DOCUMENTS 0289925 11/1988 European Pat. Off. ............ 548/544

Primary Examiner—David B. Springer
Attorney, Agent, or Firm—Curtis, Morris & Safford

[57] ABSTRACT

Chiral substituted tartarimides, a process for their preparation and their use as doping agents in liquid-crystal mixtures.

The new chiral N-substituted tartarimides which are esterified on both of the OH groups (pyrrolidinediones) are characterized by the general formula (I)

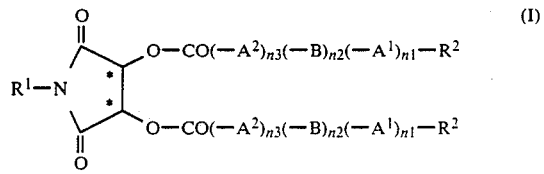

in which the symbols have the following meaning:

$R^2$ denotes linear or branched $(C_1-C_{16})$-alkyl, it being possible for one or two non-adjacent $CH_2$ groups to be replaced by O or S, or, if $n1=1$, also denotes F, Cl, Br or CN, $A^1$ and $A^2$ independently of one another denote 1,4-phenylene, diazine-2,5-diyl, diazine-3,6-diyl, 1,4-cyclohexylene, 1,3-dioxane-2,5-diyl, 1,3-dithiane-2,5-diyl or 1,4-bicyclo(2,2,2)octylene, it being also possible for these groups to be at least monosubstituted by F, Cl, Br, CN and/or $(C_1-C_{12})$-alkyl (if appropriate one or two non-adjacent $CH_2$ groups are replaced by O atoms), B denotes CO—O, O—CO, $CH_2$—$CH_2$, $OCH_2$, $CH_2O$, CH=N, N=CH or N=N, n1 and n3 independently of one another denote zero, 1 or 2, n1 and n3 not being zero at the same time, n2 denotes zero or 1, n1+n2+n3 being not more than 4, and $R^1$ denotes linear or branched $(C_1-C_{16})$-alkyl or $R^3$—$(A^1$—$)_{n1}(B$—$)_{n2}(A^2$—$)_{n3}$, in which $R^3$ is H or $R^2$.

These compounds are preferably used as doping agents in twistable liquid-crystal mixtures, in which they effect temperature compensation and twisting.

5 Claims, 2 Drawing Sheets

CHIRAL SUBSTITUTED TARTARIMIDES

Chiral substituted tartarimides, a process for their preparation and their use as doping agents in liquid-crystal mixtures.

In general, the characteristic lines of the electrooptical effects used in liquid-crystal displays change with temperature. Particularly in the case of drive in the multiplex mode, this results in difficulties which can lead to an undesirable limitation of the working temperature range. In the case of various electrooptical effects it is possible, by adding chiral compounds to the nematic liquid crystal, to influence advantageously the temperature dependence of the electrooptical characteristic lines via the temperature function of the pitch of the cholesteric helical structure induced thereby, for example in the case of the cholesteric-nematic phase transition effect, the TN (twisted nematic) cell and the recently introduced SBE (supertwisted birefringence effect). In general, the customary known doping agents induce a pitch which increases as the temperature rises; recently doping agents which do not exhibit this effect, which is often undesirable, have also been described.

Tartaric acid derivatives, such as tartaric acid diesters, diamides or dinitriles, which can be substituted on the hydroxyl groups in such a way that they are attached to mesogenic radicals via an ester group as the functional group are known from EP-A 0,234,437. The compounds are prepared, for example, by reacting a tartaric acid diester with mesogenic carboxylic acids or carboxylic acid halides. Cyclic tartaric acid derivatives (dioxolane derivatives) are also described in this EP-A, but these are formed by cyclization at the hydroxyl groups of tartaric acid diesters.

Although these tartaric acid derivatives known from the state of the art are often suitable, at comparatively low added amounts, for obtaining an optimization of the temperature compensation and a considerable twisting-expressed by the HTP (helical twisting power)=1/p.c (p=the pitch of the induced helical structure in $\mu$m and c=the concentration of the chiral doping agent in % by weight) at values of up to about 0.23 at 10—the twisting power is still too low for certain applications and/or its temperature dependence at values of a little under 1 % per K is still too high.

The object of the present invention is, therefore, to find new compounds which, when used as chiral doping agents in liquid-crystal mixtures at particularly low added amounts, on their own or as a mixture, effect an optimization of the temperature compensation and at the same time a particularly powerful twisting of the liquid-crystal mixtures; additionally it should also be possible, starting from a comparable base structure, to modify the properties of the molecule in a specific direction by minor variations in the molecule.

The invention starts from the (known) chiral substituted tartaric acid derivatives substituted by mesogenic radicals at the hydroxyl groups. The compounds according to the invention are characterized by the general formula (I)

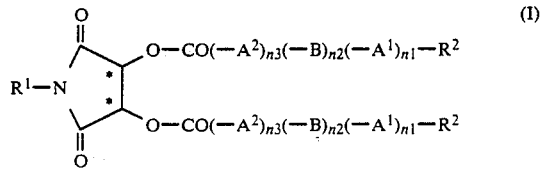

in which the symbols have the following meanings:

$R^2$ denotes linear or branched $(C_1-C_{16})$-alkyl, it being possible for one or two non-adjacent $CH_2$ groups to be replaced by O or S, or, if nl=1, also denotes F, Cl, Br or CN, $A^1$ and $A^2$ independently of one another denote 1,4-phenylene, diazine-2,5-diyl, diazine-3,6-diyl, 1,4-cyclohexylene, 1,3-dioxane-2,5-diyl, 1,3-dithiane-2,5-diyl or 1,4-bicyclo(2,2,2)octylene, it being also possible for these groups to at least monosubstituted by F, Cl, Br, CN and/or $(C_1-C_{12})$-alkyl (if appropriate one or two non-adjacent $CH_2$ groups are replaced by O atoms), B denotes CO-O, O-CO, $CH_2$-$CH_2$, $OCH_2$, $CH_2O$, CH=N, N=CH or n1 and n3 independently of one another denote zero, 1 or 2, n1 and n3 not being zero at the same time, n2 denotes zero or 1, n1+n2+n3 being not more than 4, and $R^1$ denotes linear or branched $(C_1-C_{16})$-alkyl or $R^3$—$(A^1$—$)_{n1}(B$—$)_{n2}(A^2$—$)_{n3}$, in which $R^3$ is H or $R^2$.

The compounds mentioned are chiral, N-substituted tartarimides and are esterified at both of the OH groups (pyrrolidinediones).

The object intended is also achieved by a twistable liquid-crystal mixture containing at least one chiral compound which, as a chiral compound, contains at least one compound of the general formula I. The term "twistable liquid-crystal mixture" is to be understood as meaning mixtures containing nematic, cholesteric, tilted-smectic and particularly smectic C ($S_c$ or SmC) phases.

The twistable liquid-crystal mixtures according to the invention are composed of 2 to 20, preferably 2 to 15, components, including at least one of the chiral doping agents claimed in the invention. The other constituents are preferably selected from the known compounds having nematic, cholesteric and/or tilted-smectic phases, and include, for example, Schiff's bases, biphenyls, terphenyls, phenylcyclohexanes, cyclohexylbiphenyls, pyrimidines, cinnamic acid esters, cholesterol esters or terminal-polar, multinuclear esters, bridged in various ways, of p-alkylbenzoic acids. In general, the liquid-crystal mixtures available commercially are, before the addition of the chiral doping agent, already in the form of mixtures of a very wide variety of components of which at least one is mesogenic, i.e. as a compound, in the form of derivatives or as a mixture with specific co-components, exhibits a liquid-crystal phase [=at least one enantiotropic (clear point>melting point) or monotropic (clear point<melting point) mesophase formation can be expected].

By means of the newly developed compounds as doping agents it is possible to achieve a particularly great twisting at a particularly low amount of doping agent in liquid-crystal mixtures, it being possible for the compounds on their own or as a mixture additionally to have a pitch which is essentially independent of temperature change, i.e. the increase or decrease of the pitch is, in general, within the range of less than 0.5 % per K. By suitable variation of the mesogenic radicals it is possible to induce either a right-handed or a left-handed helix or even to obtain an inversion of the helix at a specific temperature; i.e. these compounds are distinguished by the fact that the handiness of the twisting changes at a certain inversion temperature, this inversion temperature in the present case being between the solidification point and the clear point of the particular liquid-crystal mixtures; if commercially available liquid-crystal mixtures are used this means a temperature range of, especially, −40° C. to +200° C., preferably −20° C. to +140° C. A further use of the compounds according to the invention can be effected in thermotopography or for the production of "blue phases" (=cholesteric systems having a relatively small pitch, for example less than 800 nm).

Preferred compounds of the general formula I are those in which the symbols have the following meaning:
$R^2$ denotes linear ($C_4$–$C_{12}$), it being possible for the $CH_2$ group adjacent to the bonding dash leading to the next radical to be replaced by O,
$A^1$ and $A^2$ independently of one another denote 1,4-phenylene, diazine-2,5-diyl or 1,4-cyclohexylene,
B denotes CO-O or O-CO, OCH$_2$ or CH$_2$O,
n1 and n3 denote zero or 1, and
$R^1$ denotes linear ($C_1$–$C_{12}$)-alkyl or $R^3$—($A^1$—)$_{n1}$($A^2$—)$_{n3}$ in which $R^3$=H or $R^2$; $A^1$ and $A^2$=1,4-phenylene or 1,4cyclohexylene and n1 and n3 =zero or 1.

Amongst these in turn, particularly preferred compounds are those in which the symbols in the general formula have the following meanings:
$A^1$ and $A^2$ independently of one another denote 1,4-phenylene or 1,4-cyclohexylene,
B denotes CO-O or O-CO, and
n1 and n3 denote 1.

The starting compounds in the process, in which the object intended is achieved in another way, for the preparation of the compounds of the general formula (I) are the chiral N-substituted tartarimides (II)

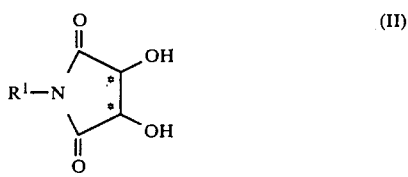

which can preferably be prepared by known reactions [A. Ladenburg, Ber. dtsch. Chem. Ges. 29, 2711 (1896) or F. Barrow et al., J. Chem. Soc. (London) 1939, 638] from tartaric acid and the corresponding primary amines; the meanings indicated above apply to $R^1$. These chiral N-substituted tartarimides of the general formula II are esterified with a suitable reactive form of a mesogenic carboxylic acid (III),

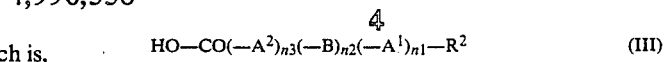

in particular with the acid halides (in this case Br or Cl instead of HO).

In general the liquid-crystal mixtures contain 0.01 to 70% by weight, in particular 0.05 to 50% by weight, of the doping agent(s) according to the invention.

EXAMPLE 1 (preparation of the tartarimide)

0.1 mol (15.0 g) of L(+)-tartaric acid is dissolved in 5 ml of hot water and 0.1 mol (12.9) g) of n-octylamine is added dropwise (at about 100° C.). A homogeneous solution is obtained by heating to about 120° C., with considerable formation of foam. The reaction mixture is then allowed to stand for about 12 hours and is then heated at about 140° C. for 8 hours; the water formed in the condensation reaction is volatized. After cooling, the liquid solidifies; the product, composed of about 28 g of a brown, viscous mass, is recrystallized 3 times from ethanol and is washed with diethyl ether. The pure product melts at 140° C. to 143° C. and has an $[\alpha]^{20°\ C.}_D$ of +117° C. in ethanol.

The other tartarimides are prepared analogously.

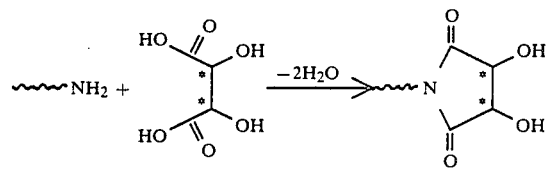

EXAMPLE 2 (general instructions for esterification)

2 mmol of the acid chloride are first put into 5 ml of anhydrous CHCl$_3$ at 3 to 5° C. 1 mmol of the tartarimide and 2 mg of dimethylaminopyridine are then dissolved in 4 ml of anhydrous pyridine and the solution is added dropwise to the acid chloride solution in the course of 10 minutes. The reaction mixture is stirred for 12 hours and the solvents are then removed by distillation (first under a water pump vacuum and then under an oil pump vacuum). The residue which remains can be separated over a flash column (40 g to 50 g of SiO$_2$, CH$_2$Cl$_2$). The doubly esterified product is dissolved twice in CH$_2$Cl$_2$ and/or diethyl ether and can then be precipitated with petroleum ether.

The following compounds are synthesized by the preparation instructions above:

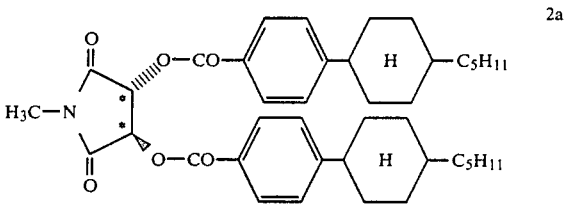

2a (3R,4R)-(+)-Methyl-3,4-bis-[4-(trans-4-n-pentylcyclohexyl)-benzoyloxy]-pyrrolidine-2,5-dione

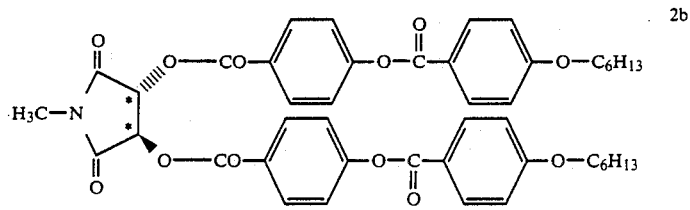

(3R,4R)-(+)-1-Methyl-3,4-bis-(4-(4-, 5n-hexyloxybenzoyloxy)-benzoyloxy-pyrrolidine-2,5-dione

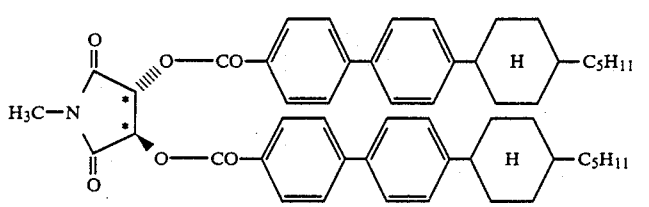

(3R,4R)-(+)-1-Methyl-3,4-bis-(4'-trans-n-pentylcyclohexyl-4-diphenylcarbonyloxy)-pyrrolidine-2,5-dione

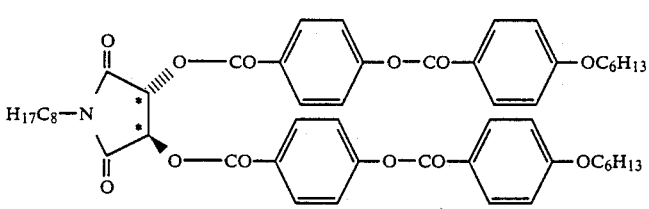

(3R,4R)-(+)-n-1-Octyl-3,4-bis-[4-(4-n-hexyloxybenzoyloxy)-benzoyloxy]-pyrrolidine-2,5-dione

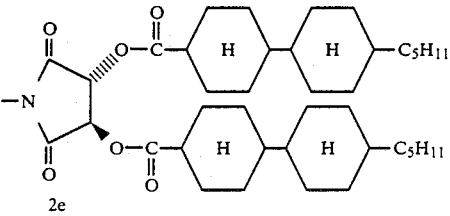

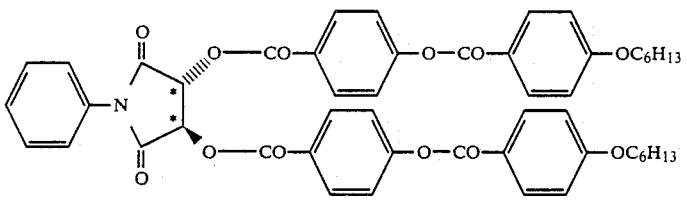

(3R,4R)-(+)-1-Phenyl-3,4-bis-[(4-(4-n-hexyloxybenzoyloxy)-benzoyloxy]-pyrrolidine-2,5-dione

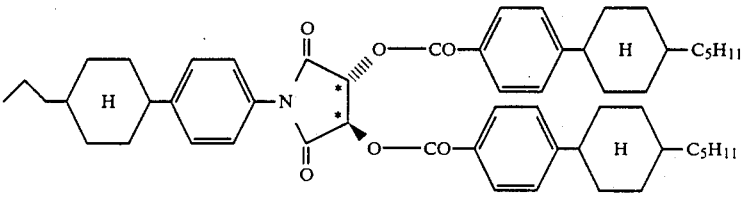

(3R,4R)-1-[4-(trans-4-n-Propylcyclohexy)-phenyl]-3,4-bis-[4-trans-4-n-pentylcyclohexy l)-benzoyloxy]-pyrrolidine-2,5-dione (3R,4R)-1-Methyl-3,4-bis(4'-trans-n-pentyl-4-transbicyclohexylcarbonyloxy)-pyrrolidine-2,5-dione

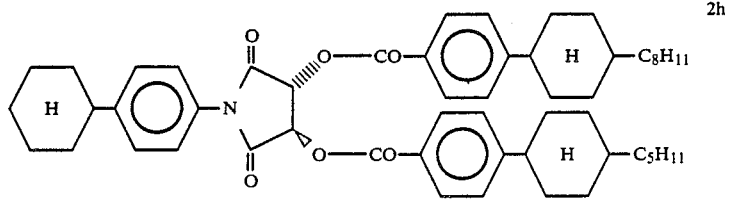

(3R,4R)-1-(4-cyclohexyl)-phenyl-3,4-bis-[(4-trans-4-n-phenyl-cyclohexyl)-benzoyloxy] pyrrolidine-dione(2,5)

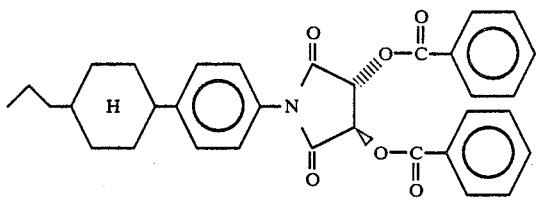

(3R,4R)-1-[4-(trans-4-n-Propyl-cyclohexyl)-phenyl]-3,4-bis(benzoyloxy) pyrrolidine-dione(2,5)

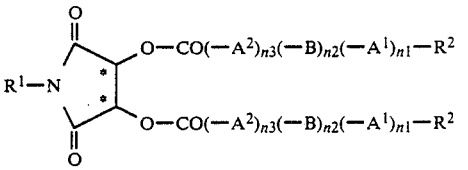

in which
R² is linear (C₄–C₁₂) alkyl, it being possible for the CH₂ group bonding to the next radical to be replaced by O,
A¹ and A² independently of one another are 1,4-phe-

TABLE

| Compound No. | Twisting power as the product of [p.c.] (μm. % by wt.) | p.c. from 10 to 100° C. | Melting point (°C.) | [α]²⁰ | concentration (g/100 ml) |
|---|---|---|---|---|---|
| 2a | −2.67 → −2.76 | 0.09 | 206 | +171° (CHCl₃) | 1.04 |
| 2b | −2.69 → −2.88 | 0.19 | 160 | +170° (CHCl₃) | 0.54 |
| 2c | −2.47 → −2.10 | 0.37 | 283 (decomp.) | +228° (CHCl₃) | 1.04 |
| 2d | −4.20 → −4.63 | 0.43 | 57–58 | +136° (CHCl₃) | 1.13 |
| 2e | −4.50 → −5.80 | 1.30 | 184–187 | +103° (CHCl₃) | 1.01 |
| 2f | +16 → −60 | * | 72 | +77° (CHCl₃) | 0.11 |
| 2g | — | — | — | — | — |
| 2h | −18.8 → 12.2 | 6.6 | 181–183 | +83° (CHCl₃) | 0.77 |
| 2i | | | 220 | +86° (CHCl₃) | 1.19 |

*Inversion of helix

Measurement of the twisting power is carried out in a commercially available nematic wide-range mixture—"RO-TN 404" made by Hoffmann-La Roche Aktiengesellschaft (Basel/Switzerland)—having a clear point of 104° C.

Figure 1B:
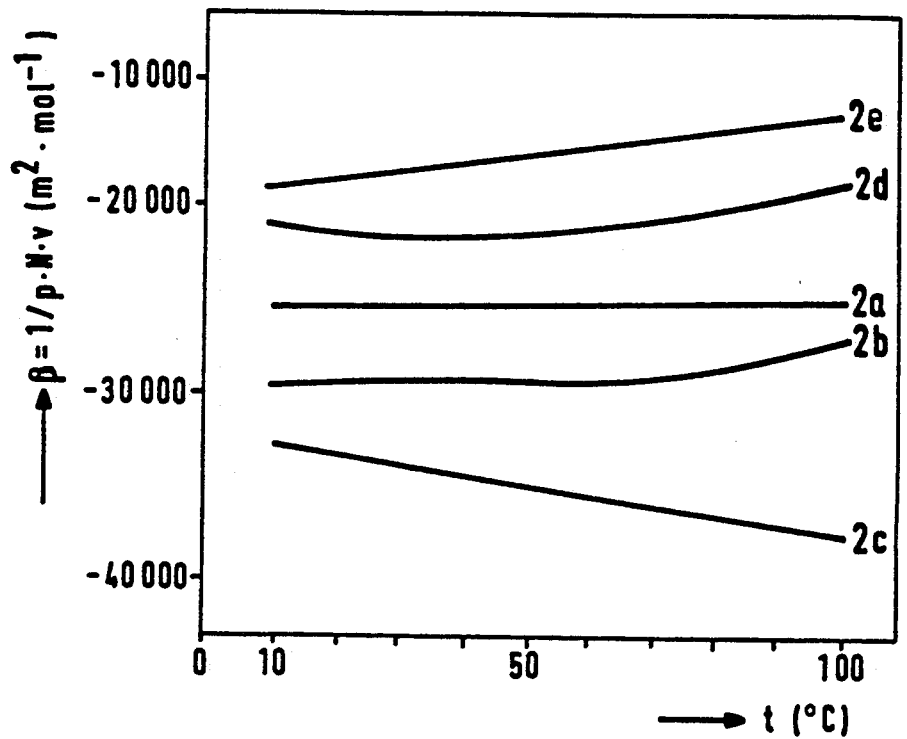
Figure 2A:
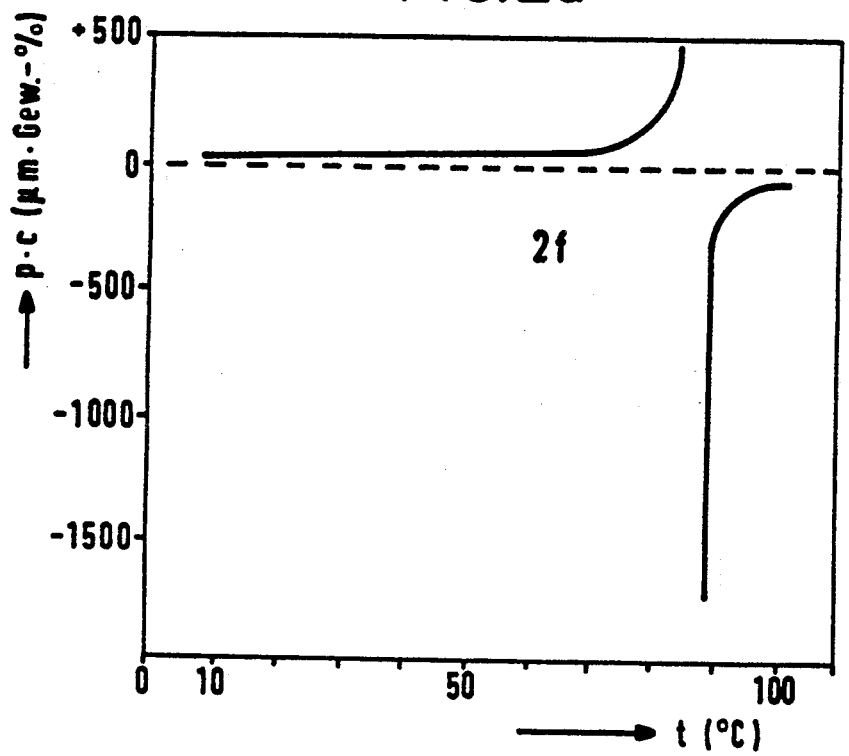
Figure 2B:
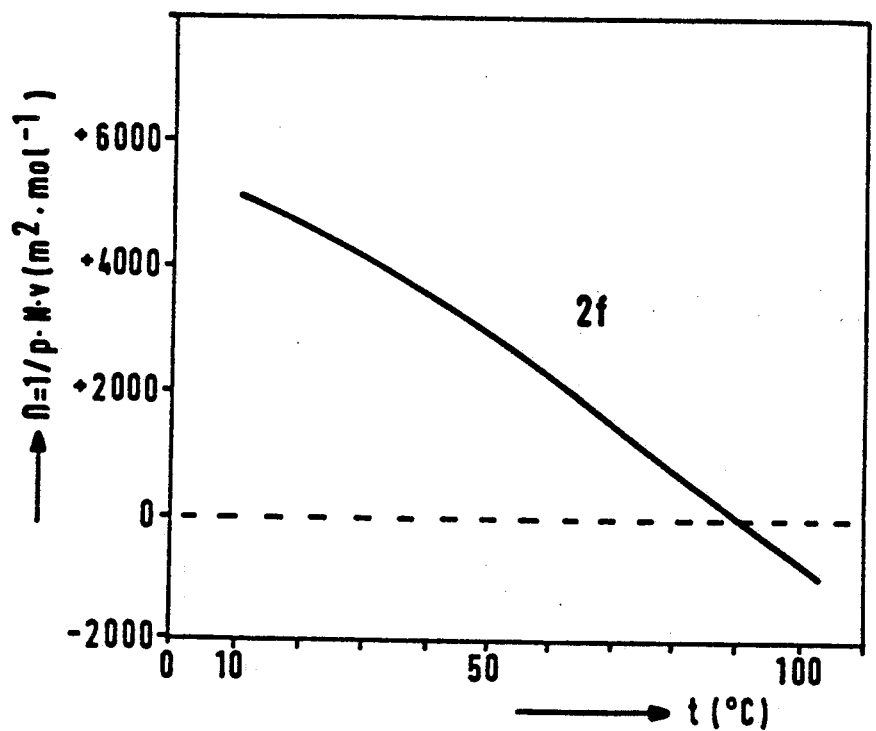

In the annexed FIGS. 1A and 1B the [p.c.] values and the MTP values [molecular twisting power $\beta=1/p.Nv$ (p= pitch in m, Nv=concentration of the chiral doping agent in mol/m³)] are plotted as a function of the temperature for the compounds 2a to 2e according to the invention; the corresponding values for the compound 2f, which exhibits inversion of the helix, are plotted in FIGS. 2A and 2B.

We claim:

1. A chiral substituted tartaric acid derivative which is substituted by mesogenic radicals on the hydroxyl groups and has the formula (I)

nylene, diazine-2,5-diyl or 1,4-cyclohexylene,
B is CO-O, C-CO, OCH₂ or CH₂O,
n1, n2, n3 independently of one another are zero or 1, n1 and n3 not being zero at the same time,
R¹ is linear (C₁–C₁₂)-alkyl or R³-(A¹-)$_{n1}$(A²-)$_{n3}$ in which R³=H or R²; A¹ and A²=1,4-phenylene or 1,4-cyclohexylene and n1 and n3=zero or 1.

2. A tartaric acid derivative as claimed in claim 1, wherein, in the formula (I),
A¹ and A² independently of one another are 1,4-phenylene or 1,4-cyclohexylene,
B is CO-O or O-CO, and n1 and n3 are 1.

3. A tartaric acid derivative as claimed in claim 1, wherein, in the formula (I), the group (—A²)$_{n3}$(—B)$_{n2}$(—A¹)$_{n1}$ is

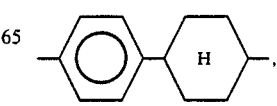

-continued

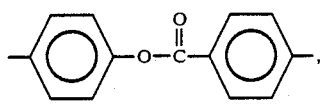

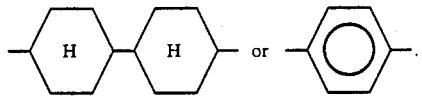

4. A tartaric acid derivative as claimed in claim 3, wherein, in the formula (I), —R¹ is

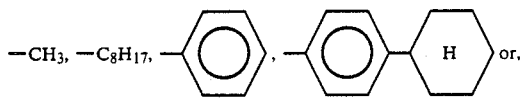

-continued

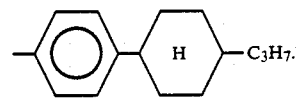

5. A tartaric acid derivative which is
(3R,4R)-(+)-1-methyl-3,4-bis-(4-(4-,5n-hexyloxybenzoyloxy)-benzoyloxy)-pyrrolidine-2,5-dione,
(3R,4R)-(+)-methyl-3,4-bis-(4-(trans-4-n-pentylcyclo-hexyl)-benzoyloxy)-pyrrolidine-2,5-dione,
(3R,4R)-(+)-methyl-3,4-bis-(4'-trans-n-pentylcyclohexyl-4-diphenylcarbonyloxy)-pyrrolidine-2,5-dione,
(3R,4R)-(+)-n-1-octyl-3,4-bis-(4-(4-n-hexyloxybenzoyloxy)-benzoyloxy)-pyrrolidine-2,5-dione,
(3R,4R)-(+)-1-phenyl-3,4-bis-(4-(4-n-hexloxybenzoyloxy)-benzoyloxy)-pyrrolidine-2,5-dione,
(3R,4R)-1-(4-(trans-4-n-propylcyclohexyl)-phenyl)-3,4-bis-(4-trans-4-n-pentylcyclohexyl)-benzoyloxy)-pyrrolidine-2,5-dione,
(3R,4R)-1-methyl-3,4-bis(4'-trans-n-pentyl-4-trans-bicyclohexylcarbonyloxy)-pyrrolidine-2,5-dione,
(3R,4R)-1-(4-cyclohexyl)-phenyl-3,4-bis-((4-trans4-n-phenyl-cyclohexyl)-benzoyloxy) pyrrolidine-dione(2,5) or
(3R,4R)-1-(4-(trans-4-n-propyl-cyclohexyl)-phenyl)-3,4-bis(benzoyloxy)pyrrolidine-dione(2,5).

* * * * *

UNITED STATES PATENT AND TRADEMARK OFFICE
CERTIFICATE OF CORRECTION

PATENT NO. : 4,996,330

DATED : February 26, 1991

INVENTOR(S) : Scherowsky et al.

It is certified that error appears in the above-identified patent and that said Letters Patent is hereby corrected as shown below:

Col. 8, claim 1, line 49;

change "C-CO" to --O-CO--.

Signed and Sealed this

Nineteenth Day of January, 1993

Attest:

DOUGLAS B. COMER

Attesting Officer     Acting Commissioner of Patents and Trademarks